(12) United States Patent
Hino (10) Patent No.: US 10,750,937 B2
(45) Date of Patent: Aug. 25, 2020

(54) STEREOSCOPIC ENDOSCOPE APPARATUS HAVING VARIABLE FOCUS AND FIXED FOCUS OBJECTIVE OPTICAL SYSTEMS

(71) Applicant: OLYMPUS CORPORATION, Tokyo (JP)

(72) Inventor: Kazuhiko Hino, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 459 days.

(21) Appl. No.: 15/796,915

(22) Filed: Oct. 30, 2017

(65) Prior Publication Data

US 2018/0042465 A1 Feb. 15, 2018

Related U.S. Application Data

(63) Continuation of application No. PCT/JP2016/061712, filed on Apr. 11, 2016.

(30) Foreign Application Priority Data

May 12, 2015 (JP) ................................. 2015-097683

(51) Int. Cl.
*A61B 1/00* (2006.01)
*A61B 1/04* (2006.01)
(Continued)

(52) U.S. Cl.
CPC ............ *A61B 1/00193* (2013.01); *A61B 1/00* (2013.01); *A61B 1/00009* (2013.01);
(Continued)

(58) Field of Classification Search
None
See application file for complete search history.

(56) References Cited

U.S. PATENT DOCUMENTS

| | | | | |
|---|---|---|---|---|
| 5,860,912 A | * | 1/1999 | Chiba | A61B 1/00059 600/111 |
| 2003/0191364 A1 | * | 10/2003 | Czarnek | A61B 1/00193 600/111 |

(Continued)

FOREIGN PATENT DOCUMENTS

| | | |
|---|---|---|
| EP | 1685788 A1 | 8/2006 |
| EP | 2563022 A1 | 2/2013 |

(Continued)

OTHER PUBLICATIONS

Machine English Translation of JP 2006093860 A, Yoshida Hideaki, Apr. 6, 2006.*

(Continued)

*Primary Examiner* — John P Leubecker
*Assistant Examiner* — Minqiao Huang
(74) *Attorney, Agent, or Firm* — Scully, Scott, Murphy & Presser, P.C.

(57) ABSTRACT

A stereoscopic endoscope apparatus includes: an insertion portion; a variable focus objective optical system; a fixed focus objective optical system; an image pickup section; an image signal generation output section that outputs an image signal for two-dimensional display when a focal length of the variable focus objective optical system and a focal length of the fixed focus objective optical system are different from each other, and outputs an image signal for stereoscopic observation when the focal length of the variable focus objective optical system and the focal length of the fixed focus objective optical system are coincident with each other in the near point observation state.

11 Claims, 4 Drawing Sheets

(51) Int. Cl.

| | | |
|---|---|---|
| G02B 23/24 | (2006.01) | |
| H04N 5/225 | (2006.01) | |
| G03B 19/07 | (2006.01) | |
| G03B 35/08 | (2006.01) | |
| G03B 35/00 | (2006.01) | |
| H04N 5/232 | (2006.01) | |
| G02B 7/28 | (2006.01) | |
| H04N 5/235 | (2006.01) | |

(52) U.S. Cl.
CPC ........ *A61B 1/0019* (2013.01); *A61B 1/00045* (2013.01); *A61B 1/00188* (2013.01); *A61B 1/04* (2013.01); *G02B 7/28* (2013.01); *G02B 23/24* (2013.01); *G03B 19/07* (2013.01); *G03B 35/00* (2013.01); *G03B 35/08* (2013.01); *H04N 5/2251* (2013.01); *H04N 5/232* (2013.01); *H04N 5/235* (2013.01); *H04N 5/23212* (2013.01)

(56) References Cited

U.S. PATENT DOCUMENTS

| | | | |
|---|---|---|---|
| 2004/0002627 A1* | 1/2004 | Igarashi | A61B 1/00193 600/166 |
| 2004/0199061 A1 | 10/2004 | Glukhovsky | |
| 2006/0126176 A1* | 6/2006 | Nogami | A61B 1/0005 359/464 |
| 2006/0209185 A1* | 9/2006 | Yokoi | A61B 1/00016 348/65 |
| 2007/0058249 A1* | 3/2007 | Hirose | G02B 21/22 359/464 |
| 2012/0113509 A1* | 5/2012 | Yamada | G03B 35/08 359/462 |
| 2012/0188347 A1* | 7/2012 | Mitchell | A61B 1/00193 348/50 |
| 2013/0038700 A1* | 2/2013 | Horita | H04N 13/246 348/47 |
| 2014/0039257 A1* | 2/2014 | Higuchi | G02B 7/34 600/109 |
| 2014/0210945 A1* | 7/2014 | Morizumi | H04N 13/239 348/45 |
| 2015/0018617 A1* | 1/2015 | Aono | A61B 1/00142 600/111 |
| 2015/0073209 A1* | 3/2015 | Ikeda | A61B 1/0005 600/103 |
| 2015/0092023 A1* | 4/2015 | Asakura | G03B 35/08 348/49 |
| 2016/0259159 A1* | 9/2016 | Matsui | G02B 23/26 |

FOREIGN PATENT DOCUMENTS

| | | |
|---|---|---|
| JP | H08262333 A | 10/1996 |
| JP | H09005643 A | 1/1997 |
| JP | 2004536648 A | 12/2004 |
| JP | 2005143991 A | 6/2005 |
| JP | 2006093860 A | 4/2006 |
| JP | 2014140593 A | 8/2014 |
| WO | 2003011103 A2 | 2/2003 |
| WO | 2005048825 A1 | 6/2005 |
| WO | 2011132552 A1 | 10/2011 |

OTHER PUBLICATIONS

International Search Report dated Jul. 12, 2016 issued in PCT/JP2016/061712.

Japanese Office Action dated Jan. 10, 2017 issued in JP 2016-563154.

* cited by examiner

STEREOSCOPIC ENDOSCOPE APPARATUS HAVING VARIABLE FOCUS AND FIXED FOCUS OBJECTIVE OPTICAL SYSTEMS

CROSS REFERENCE TO RELATED APPLICATION

This application is a continuation application of PCT/JP2016/061712 filed on Apr. 11, 2016 and claims benefit of Japanese Application No. 2015-097683 filed in Japan on May 12, 2015, the entire contents of which are incorporated herein by this reference.

BACKGROUND OF THE INVENTION

1. Field of the Invention

The present invention relates to a stereoscopic endoscope apparatus.

2. Description of the Related Art

Conventionally, endoscope apparatuses have been widely used in medical fields and the like. Endoscope apparatuses include a stereoscopic endoscope as disclosed in Japanese Patent Application Laid-Open Publication No. 8-262333. In the stereoscopic endoscope, two optical systems that are allowed to have an angle of convergence (angle formed by the lines of sight of left and right eyes) are arranged at the distal end portion of the endoscope, and two intra-subject images having parallax are picked up, to perform stereoscopic observation of an inside of a subject.

The stereoscopic endoscope disclosed in the Japanese Patent Application Laid-Open Publication No. 8-262333 is a fixed focus type. A stereo camera of a variable focus type that is capable of performing stereoscopic viewing is disclosed in the publication No. WO 2011/132552.

In endoscopic diagnosis in a human body, in particular, in fields of digestive organs, a screening examination by a far point observation and close examination of details by a near point observation are performed with one variable focus type endoscope capable of performing planar viewing.

With regard to the close examination of details by the near point observation, observation accuracy can be more improved if observation with stereoscopic viewing is possible instead of the observation with planar viewing.

SUMMARY OF THE INVENTION

A stereoscopic endoscope apparatus according to one aspect of the present invention includes: an insertion portion to be inserted into a subject; a variable focus objective optical system arranged in a distal end portion of the insertion portion, a focal length of the variable focus objective optical system being changeable between a far point observation state and a near point observation state, the variable focus objective optical system forming an optical image of the subject; a fixed focus objective optical system arranged in the distal end portion of the insertion portion, a focal length of the fixed focus objective optical system being fixed to a focal length equal to the focal length of the variable focus objective optical system in the near point observation state, the fixed focus objective optical system forming an optical image having parallax with respect to the optical image formed by the variable focus objective optical system in the near point observation state; an image pickup section that picks up the optical image formed by the variable focus objective optical system and the optical image formed by the fixed focus objective optical system; an image signal generation output section configured to output an image signal for two-dimensional display generated based on an image pickup signal obtained by picking up the optical image formed by the variable focus objective optical system by the image pickup section when the focal length of the variable focus objective optical system and the focal length of the fixed focus objective optical system are different from each other, and output an image signal for stereoscopic observation generated based on both the image pickup signal obtained by picking up the optical image formed by the variable focus objective optical system by the image pickup section and an image pickup signal obtained by picking up the optical image formed by the fixed focus objective optical system by the image pickup section when the focal length of the variable focus objective optical system and the focal length of the fixed focus objective optical system are coincident with each other in the near point observation state.

DETAILED DESCRIPTION OF THE PREFERRED EMBODIMENTS

Hereinafter, embodiments of the present invention will be described with reference to drawings.

First Embodiment (Configuration)

Figure 1:
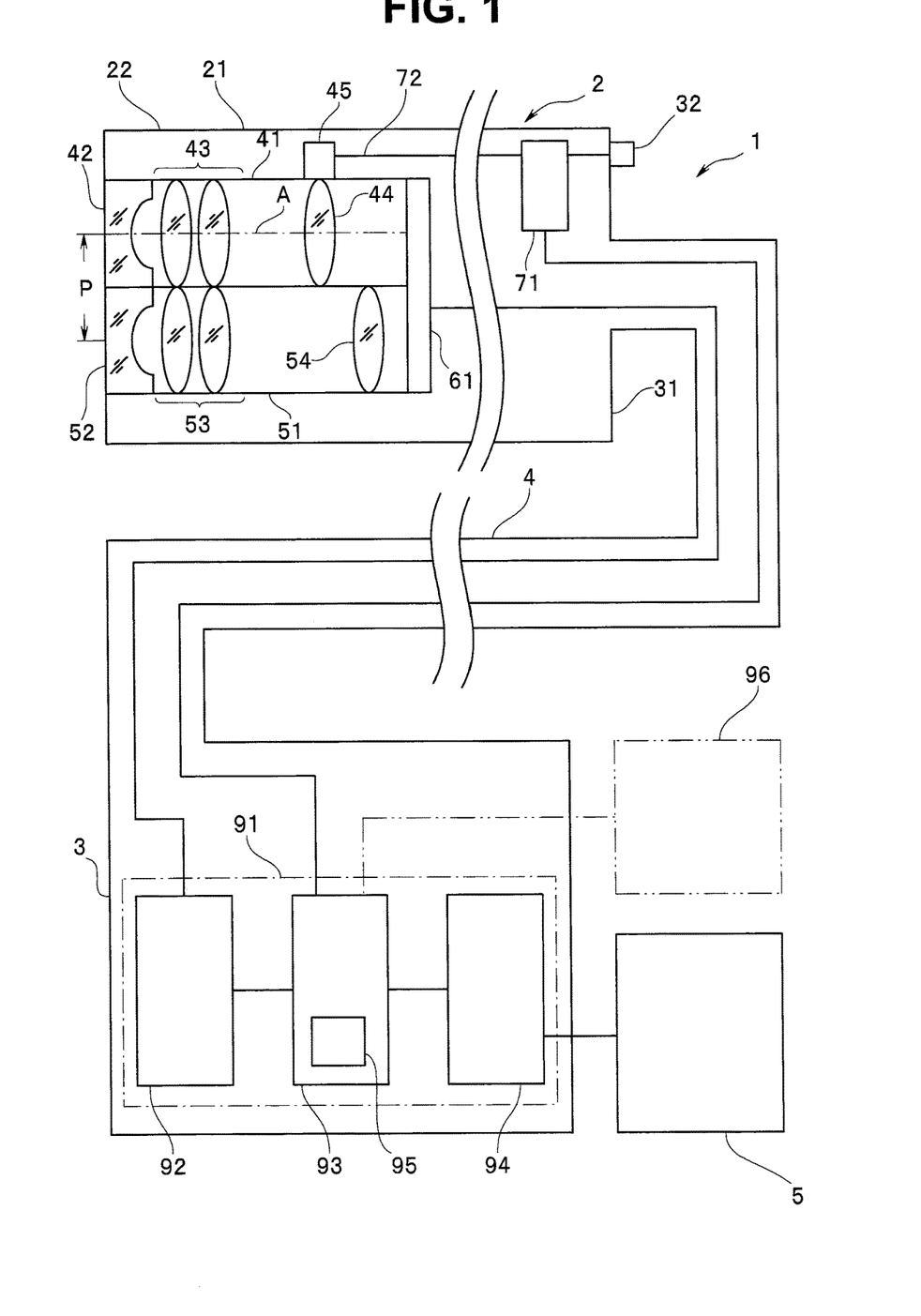
FIG. 1 is a configuration diagram of a stereoscopic endoscope apparatus according to a first embodiment of the present invention.

FIG. 1 is a configuration diagram of a stereoscopic endoscope apparatus 1 according to a first embodiment of the present invention. As shown in FIG. 1, the stereoscopic endoscope apparatus 1 is configured of a stereoscopic endoscope (hereinafter, referred to as "endoscope 2"), and a main body section 3. The endoscope 2 and the main body section 3 are connected to each other with a cable 4.

The endoscope 2 includes an insertion portion 21 to be inserted into a subject and an endoscope operation portion 31 through which an operator operates the endoscope 2.

A variable focus objective optical system 41, a fixed focus objective optical system 51, and an image pickup section 61 are provided in a distal end portion 22 of the insertion portion 21. Note that FIG. 1 omits the illustration of constituent elements in the distal end portion 22 of the insertion portion 21, except for the variable focus objective optical system 41, the fixed focus objective optical system 51, and the image pickup section 61.

Figure 2:
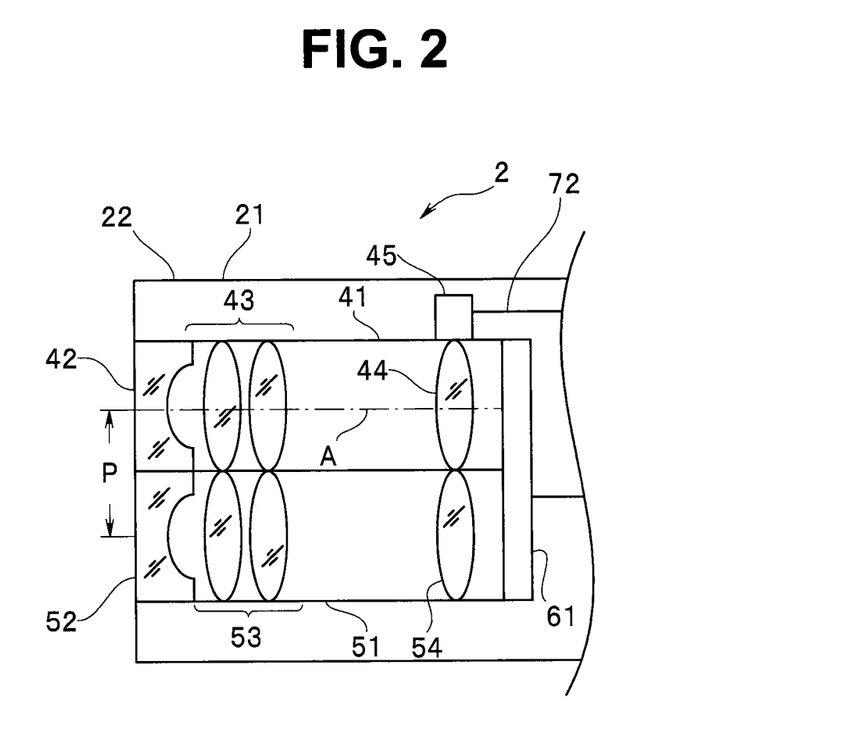
FIG. 2 is an explanatory diagram for describing a state of a variable focus objective optical system and a fixed focus objective optical system in a distal end portion in a near point observation state of the stereoscopic endoscope apparatus according to the first embodiment of the present invention.

FIG. 2 is an explanatory diagram for describing a state of the variable focus objective optical system 41 and the fixed focus objective optical system 51 in the distal end portion 22 in a near point observation state of the stereoscopic endoscope apparatus 1 according to the first embodiment of the present invention.

The variable focus objective optical system 41 is an optical system which is arranged in the distal end portion 22 of the insertion portion 21, and whose focal length can be changed. The variable focus objective optical system 41 includes a forward observation window 42 which is a lens that takes in reflection light from an inside of a subject, and also includes an optical lens group 43 and a movable lens 44 behind the forward observation window 42.

The optical lens group 43 is configured of various kinds of optical lenses that are arranged in a fixed manner.

The movable lens 44 is arranged at the rear of the optical lens group 43 so as to be movable in a direction along an optical axis A. The movable lens 44 is fixed to and supported by a lens supporting portion 45. The lens supporting portion 45 of the movable lens 44 is connected to a focus adjustment section 71 to be described later with a shape-memory alloy wire 72.

The variable focus objective optical system 41 is configured such that the focal length thereof becomes long when the movable lens 44 is positioned close to the forward observation window 42, while the focal length thereof becomes short when the movable lens 44 is positioned close to the image pickup section 61 to be described later. Therefore, in the endoscope 2, when the variable focus objective optical system 41 is brought into a near point observation state, the movable lens 44 moves to a predetermined position close to the image pickup section 61, as shown in FIG. 2.

The depth of field of the variable focus objective optical system 41 is set to be 2 mm to 3 mm in the near point observation state where the focal length is the shortest, and set to be 7 mm to 100 mm in the far point observation state where the focal length is the longest, for example.

The fixed focus objective optical system 51 is arranged in parallel with the variable focus objective optical system 41 in the distal end portion 22 of the insertion portion 21, and the focal length of the fixed focus objective optical system 51 is fixed to a predetermined focal length within a changeable range of the focal length of the variable focus objective optical system. The fixed focus objective optical system 51 includes a forward observation window 52 that takes in reflection light from the inside of the subject, and also includes an optical lens group 53 and a fixed lens 54 at the rear of the forward observation window 52.

The optical lens group 53 is configured of various kinds of optical lenses that are arranged in a fixed manner.

An interval P between the center of the forward observation window 42 of the variable focus objective optical system 41 and the center of the forward observation window 52 of the fixed focus objective optical system 51 is an interval suitable for the near point observation and set to be a range from 0.5 mm to 2 mm, for example.

The fixed lens 54 is arranged in a fixed manner at the rear of the optical lens group 53.

The predetermined focal length of the fixed focus objective optical system 51 is same as the focal length of the variable focus objective optical system 41 in the near point observation state. In addition, the depth of field of the fixed focus objective optical system 51 is set to be 2 mm to 3 mm, which is same as the depth of field of the variable focus objective optical system 41 in the near point observation state. Therefore, the stereoscopic endoscope apparatus 1 is capable of acquiring two intra-subject images having parallax for displaying an image for three-dimensional display from one same subject in the near point observation state.

The stereoscopic endoscope apparatus 1 is configured to be capable of acquiring an image for right eye from the variable focus objective optical system 41 and acquiring an image for left eye from the fixed focus objective optical system 51 in the near point observation state. Note that if the arranging positions of the variable focus objective optical system 41 and the fixed focus objective optical system 51 are reversed, the stereoscopic endoscope apparatus 1 may be configured to be capable of acquiring the image for right eye from the fixed focus objective optical system 51 and acquiring the image for left eye from the variable focus objective optical system 41.

The image pickup section 61 is configured of a device capable of performing photoelectric conversion, such as CCD (charge coupled device), for example. The image pickup section 61 is arranged at a position where reflection light returned from the subject and passed through the variable focus objective optical system 41 and reflection light returned from the subject and passed through the fixed focus objective optical system 51 are projected. The image pickup section 61 photoelectrically converts two optical images formed respectively by the reflection light projected from the variable focus objective optical system 41 and the reflection light projected from the fixed focus objective optical system 51 into image pickup signals, to output the image pickup signals to a camera control unit (hereinafter, referred to as "CCU") 92 through the cable 4.

The endoscope operation portion 31 is provided with an operation lever 32 and a focus adjustment section 71. Note that FIG. 1 omits the illustration of constituent elements in the endoscope operation portion 31, except for the operation lever 32 and the focus adjustment section 71.

An operator can input a focus adjustment instruction such as an instruction for elongating or shortening the focal length of the variable focus objective optical system 41 into the operation lever 32. The operation lever 32 is electrically connected to the focus adjustment section 71, and transmits the focus adjustment instruction by the operator to the focus adjustment section 71 as an operation signal.

The focus adjustment section 71 includes, for example, an electric actuator, and configured to be capable of adjusting the focal length of the variable focus objective optical system 41 based on the focus adjustment instruction by the operator.

The actuator includes the shape-memory alloy wire 72 connected to the lens supporting portion 45, for example. The shape-memory alloy wire 72 extends and contracts by the temperature of the shape-memory alloy wire 72 itself. When receiving the operation signal from the operation lever 32, the actuator applies electric current to the shape-memory alloy wire 72, to change the temperature of the shape-memory alloy wire 72 itself by Joule heat, thereby being capable of causing the shape-memory alloy wire 72 to extend or contract and causing the movable lens 44 to move along the optical axis A.

The focus adjustment section 71 is electrically connected to a control section 93 to be described later. The focus adjustment section 71 is configured to be capable of transmitting a setting signal indicating that the variable focus objective optical system 41 is in the near point observation state to the control section 93 when the movable lens 44 is located at a predetermined position close to the image pickup section 61 (that is, the variable focus objective optical system 41 is in the near point observation state). In addition, the focus adjustment section 71 is configured to be capable of transmitting a setting signal indicating that the variable focus objective optical system 41 is in a middle-far point observation state to the control section 93, when the movable lens 44 is not located at the predetermined position close to the image pickup section 61 (that is, the variable focus objective optical system 41 is in the middle-far point observation state other than the near point observation state).

As described above, the endoscope 2 includes, inside the distal end portion 22 of the insertion portion 21, the variable focus objective optical system 41 whose focal length is changeable, the fixed focus objective optical system 51 whose focal length is fixed, the image pickup section 61, and the focus adjustment section 71. The endoscope 2 is configured to be capable of acquiring an intra-subject image in focus by the variable focus objective optical system 41 in the middle-far point observation state, and capable of acquiring two intra-subject images in focus, which have parallax, from the same one subject by the variable focus objective optical system 41 and the fixed focus objective optical system 51 in the near point observation state.

The main body section 3 includes a processor 91. The processor 91 includes the CCU 92, the control section 93, and an image signal generation output section 94. Note that FIG. 1 omits the illustration of constituent elements in the main body section 3 except for the processor 91. In addition, the main body section 3 is connected with a monitor 5 for displaying an observation image.

The CCU 92 is electrically connected to the image pickup section 61 through the cable 4. The CCU 92 acquires an image pickup signal from the image pickup section 61, performs noise removal, various kinds of correction processing and the like on the image pickup signal, for example, and then generates a signal of an image, such as a video signal. The CCU 92 is electrically connected to the control section 93, and capable of outputting the generated signal of the image to the control section 93.

The image pickup signal acquired by the CCU 92 from the image pickup section 61 includes an image pickup signal of the optical image formed by the variable focus objective optical system 41 and the image pickup signal of the optical image formed by the fixed focus objective optical system 51. In addition, the signal of the image, which is outputted from the CCU 92 to the control section 93, includes the signal of the image acquired by the variable focus objective optical system 41 and the signal of the image acquired by the fixed focus objective optical system 51 that have been generated in the CCU 92.

The control section 93 includes a central processing unit (CPU) and a storing section (ROM, RAM, etc.), which are not shown.

The control section 93 is electrically connected to the focus adjustment section 71, the CCU 92, and the image signal generation output section 94.

The control section 93 acquires from the CCU 92 the signal of the image acquired by the variable focus objective optical system 41 and the signal of the image acquired by the fixed focus objective optical system 51.

The control section 93 includes a determination section 95. The determination section 95 reads the setting signal transmitted from the focus adjustment section 71 to the control section 93, to be capable of determining whether the variable focus objective optical system 41 is in the near point observation state.

The control section 93 is configured to be capable of outputting a control signal for instructing generation of an image for two-dimensional display and the signal of the image acquired by the variable objective optical system 41 to the image signal generation output section 94 when the determination section 95 determines that the variable focus objective optical system 41 is in the state other than the near point observation state (that is, middle-far point observation state). In this case, the signal of the image acquired by the fixed focus objective optical system 51 is not transmitted to the image signal generation output section 94.

The control section 93 is configured to be capable of outputting a control signal for instructing generation of an image for three-dimensional display, the signal of the image acquired by the variable focus objective optical system 41, and the signal of the image acquired by the fixed focus objective optical system 51 to the image signal generation output section 94 when the determination section 95 determines that the variable focus objective optical system 41 is in the near point observation state.

Figure 3:
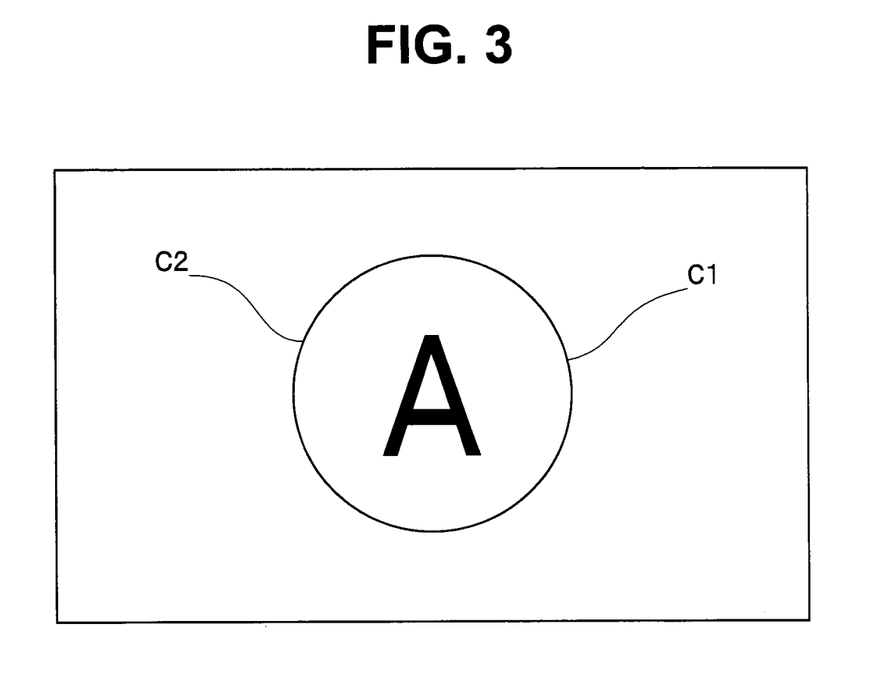
FIG. 3 is a schematic view of a display image on a monitor in a middle-far point observation state of the stereoscopic endoscope apparatus according to the first embodiment of the present invention.

FIG. 3 is a schematic view of the display image on the monitor 5 in the middle-far point observation state of the stereoscopic endoscope apparatus 1 according to the first embodiment of the present invention. Since an image for right eye C1 and an image for left eye C2 which are acquired by the variable focus objective optical system 41 do not have parallax, the images are displayed in a manner that one of the images is superimposed on the other and schematically shown with a circle including the character "A" in FIG. 3.

Figure 4:
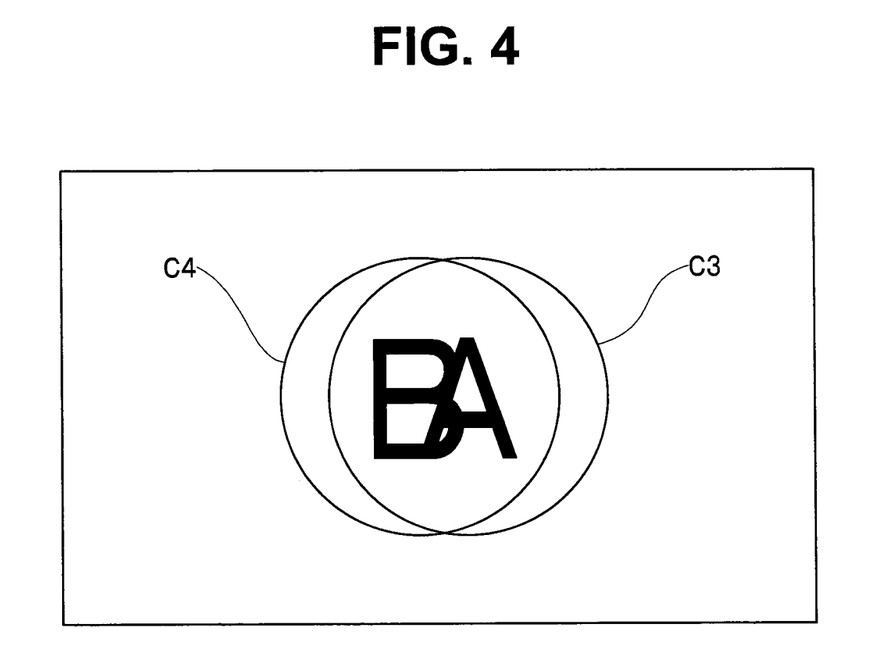
FIG. 4 is a schematic view of a display image on the monitor in the near point observation state of the stereoscopic endoscope apparatus according to the first embodiment of the present invention.

FIG. 4 is a schematic view of the display image on the monitor 5 in the near point observation state in the stereoscopic endoscope apparatus 1 according to the first embodiment of the present invention. FIG. 4 illustrates the state where the two images having parallax are displayed on the monitor 5. An image for right eye C3 acquired by the variable focus objective optical system 41 is schematically shown with the circle including the character "A", and an image for left eye C4 acquired by the fixed focus objective optical system 51 is schematically shown with the circle including the character "B".

Based on the signal of the image acquired from the image pickup section 61, when the focal length of the variable focus objective optical system 41 and the focal length of the fixed focus objective optical system 51 are different from each other, the image signal generation output section 94 outputs, as the signal of the image, the intra-subject image acquired by the variable focus objective optical system 41, and when the focal length of the variable focus objective optical system 41 and the focal length of the fixed focus objective optical system 51 are coincident with each other, the image signal generation output section 94 outputs the two intra-subject images acquired by the variable focus objective optical system 41 and the fixed focus objective optical system 51, as the signal of the image, that is, as the signal of the image for three-dimensional display.

That is, when the focal length of the variable focus objective optical system 41 and the focal length of the fixed focus objective optical system 51 are coincident with each other, the image signal generation output section 94 automatically switches the signal of the image to the signal of the image that is adaptable to the stereoscopic observation and outputs the switched signal of the image.

The image signal generation output section 94 is connected to the monitor 5 that displays the observation image.

The image signal generation output section 94 acquires the signal of the image based on the image pickup signal outputted from the image pickup section 61, through the CCU 92 and the control section 93. In addition, the image signal generation output section 94 acquires the control signal from the control section 93.

When the control signal acquired from the control section 93 is the control signal for instructing the generation of the image for two-dimensional display, the image signal generation output section 94 generates the signal of two-dimensional display for displaying the image acquired by the variable focus objective optical system 41 as the image for right eye C1 and the image for left eye C2, and outputs the generated signal of two-dimensional display to the monitor 5.

The image for right eye C1 and the image for left eye C2 that are acquired by the variable focus objective optical system 41 in the image for two-dimensional display are the same images without parallax.

When the control signal acquired from the control section 93 is the control signal for instructing the generation of the image for three-dimensional display, the image signal generation output section 94 generates a signal of the image for three-dimensional display for displaying the image acquired by the variable focus objective optical system 41 as the image for right eye C3 and the image acquired by the fixed focus objective optical system 51 as the image for left eye C4, and outputs the generated signal of the image for three-dimensional display to the monitor 5.

Note that if the arranging positions of the variable focus objective optical system 41 and the fixed focus objective optical system 51 are reversed, the image acquired by the variable focus objective optical system 41 is displayed as the image for left eye C4 and the image acquired by the fixed focus objective optical system 51 is displayed as the image for right eye C3.

The image for right eye C3 acquired by the variable focus objective optical system 41 and the image for left eye C4 acquired by the fixed focus objective optical system 51 in the image for three-dimensional display are images with parallax that are acquired from the inside of the same one subject.

The monitor 5 displays an image based on the signal of the image which is transmitted from the image signal generation output section 94. The operator puts on stereoscopic viewing glasses such as polarized glasses, for example, to thereby be able to observe the image for three-dimensional display with binocular parallax of left and right eyes displayed on the monitor 5 or the image for two-dimensional display without binocular parallax of left and right eyes displayed on the monitor 5.

(Working)

Hereinafter, working of the apparatus according to the first embodiment will be described.

When the operator gives an instruction for starting observation with a start button or the like, not shown, in the stereoscopic endoscope apparatus 1, the central processing unit (CPU) of the control section 93 reads a program that configures the determination section 95 and other processing programs, setting data, and the like, from the storing section, to start processing.

The operator puts on the stereoscopic viewing glasses.

The operator inserts the insertion portion 21 of the endoscope 2 into a subject for performing a screening examination of an observation site from a remote position. When inserting the insertion portion 21 of the endoscope 2 into the subject, the operator operates the operation lever 32, to bring the variable focus objective optical system 41 into the middle-far point observation state.

The focus adjustment section 71 transmits the setting signal for informing that the variable focus objective optical system 41 is in the middle-far point observation state to the control section 93.

The control section 93 receives the setting signal informing that the variable focus objective optical system 41 is in the middle-far point observation state from the focus adjustment section 71, and outputs the control signal for instructing the generation of the image for two-dimensional display and the signal of the image acquired from the variable focus objective optical system 41 to the image signal generation output section 94. The image signal generation output section 94 generates, from the signal of the image acquired from the variable focus objective optical system 41, which has been acquired from the control section 93, the signal of the image for right eye C1 and the signal of the image for left eye C2 which is the same image as the image for right eye C1, as the signal of the image for two-dimensional display, to output the signal of the image for two-dimensional display to the monitor 5.

The monitor 5 acquires the signal of the image for two-dimensional display from the image signal generation output section 94, to display the image for two-dimensionally display.

The signal of the image for right eye C1 and the signal of the image for left eye C2 are generated as the signal of the image for two-dimensional display and outputted to the monitor 5, which enables the operator to observe the image for two-dimensional display displayed on the monitor 5, with the stereoscopic viewing glasses put on.

The operator putting on the stereoscopic viewing glasses operates the operation lever 32, to adjust the focal length of the variable focus objective optical system 41 to cause the variable focus objective optical system 41 to focus on the observation site, while viewing the image for two-dimensional display displayed on the monitor 5. As a result, the image for two-dimensional display (FIG. 3) of the observation site observed from the remote position is displayed on the monitor 5 in a focused state. The operator performs screening examination of the observation site from the remote position, while viewing the monitor 5.

After the screening examination, in order to perform close examination of the observation site from a near position, the operator brings the endoscope 2 close to the observation site, operates the operation lever 32 of the focus adjustment section 71, and brings the variable focus objective optical system 41 into the near point observation state, with the stereoscopic viewing glasses put on.

The focus adjustment section 71 transmits the setting signal informing that the variable focus objective optical system 41 is in the near point observation state to the control section 93.

The control section 93 receives the setting signal informing that the variable focus objective optical system 41 is in the near point observation state from the focus adjustment section 71, and outputs the control signal for instructing the generation of the image for three-dimensional display, the signal of the image acquired from the variable focus objective optical system 41, and the signal of the image acquired from the fixed focus objective optical system 51 to the image signal generation output section 94.

The image signal generation output section 94 receives the control signal for instructing the generation of the image for three-dimensional display from the control section 93, to generate the signal of the image for right eye C3 based on the signal of the image acquired from the variable focus objective optical system 41 and the signal of the image for left eye C4 based on the signal of the image acquired from the fixed focus objective optical system, as the signal of the image for three-dimensional display, and outputs the generated signal of the image for three-dimensional display to the monitor 5.

The monitor 5 acquires the signal of the image for three-dimensional display from the image signal generation output section 94 and displays the image for three-dimensional display.

The operator putting on the stereoscopic viewing glasses observes the observation site from the near position by stereoscopic viewing, while viewing the monitor 5.

According to the above-described first embodiment, the stereoscopic endoscope apparatus 1 is capable of changing the focal length, and displaying the image for two-dimensional display when observing a middle-far point, and switching the image automatically to the image for three-dimensional display to display the image for three-dimensional display when observing the near point.

Second Embodiment

In the first embodiment, the determination section 95 reads the signal transmitted from the focus adjustment section 71 to determine whether the variable focus objective optical system 41 is in the near point observation state. In the second embodiment, the determination section 95 detects whether the fixed focus objective optical system 51 is focused on the observation site based on the image acquired by the fixed focus objective optical system 51, to determine whether the variable focus objective optical system 41 is in the near point observation state. Note that description on the same configurations as those in the first embodiment will be omitted.

Figure 5:
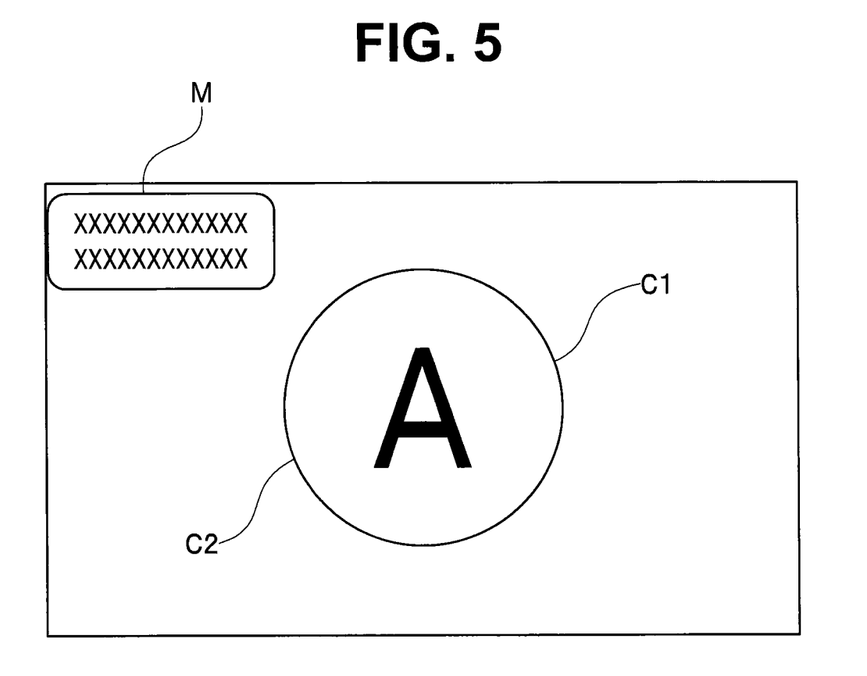
FIG. 5 is a schematic view showing a state where a message is displayed on a monitor of a stereoscopic endoscope apparatus according to a second embodiment of the present invention.

FIG. 5 is a schematic view showing the state where the message M is displayed on the monitor 5 of a stereoscopic endoscope apparatus 1 according to the second embodiment of the present invention.

The determination section 95 is configured to be capable of determining whether the fixed focus objective optical system 51 is focused on the observation site when the image for two-dimensional display is displayed. The determination section 95 extracts high-frequency components from the image acquired by the fixed focus objective optical system 51, calculates a contrast evaluation value by integrating the high-frequency components, and determines whether the fixed focus objective optical system 51 is focused on the observation site by evaluating the contrast evaluation value.

When the determination section 95 determines that the fixed focus objective optical system 51 is focused on the observation site when the image for two-dimensional display is displayed, the control section 93 generates the message M for informing the operator that the image is switchable to the image for three-dimensional display, to add the generated message M to the image acquired from the variable focus objective optical system 41, and outputs the signal of the image to which the message M is added to the image signal generation output section 94.

The image signal generation output section 94 acquires from the control section 93 the signal of the image to which the message M is added, generates the signal of the image for two-dimensional display, and outputs the generated signal of the image for two-dimensional display to the monitor 5.

The monitor 5 acquires from the image signal generation output section 94 the signal of the image for two-dimensional display to which the message M is added, to display the image for two-dimensional display to which the message M is added.

After the message M is displayed on the monitor 5, when the operator gives an instruction for displaying the image for three-dimensional display through the main body operation section 96, the control section 93 outputs the control signal for instructing the generation of the image for three-dimensional display, the signal of the image acquired by the variable focus objective optical system 41, and the signal of the image acquired by the fixed focus objective optical system 51 to the image signal generation output section 94.

The image signal generation output section 94 receives the control signal for instructing the generation of the image for three-dimensional display from the control section 93, to generate the image for right eye C3 based on the image acquired from the variable focus objective optical system 41 and the image for left eye C4 based on the image acquired by the fixed focus objective optical system 51, as the image for three-dimensional display. The image signal generation output section 94 converts the image for three-dimensional display constituted of the image for right eye C3 and the image for left eye C4 into a signal, and then outputs the signal to the monitor 5.

The monitor 5 acquires the signal of the image for three-dimensional display from the image signal generation output section 94, and displays the image for three-dimensional display on the monitor 5.

With such a configuration, determination is made based on whether the fixed focus objective optical system 51 is actually focused on the observation site. Therefore, the image in focus is acquired from the fixed focus objective optical system 51, to thereby enable more highly precise determination to be made on whether the stereoscopic viewing display is possible.

In addition, with such a configuration, when the stereoscopic viewing display becomes possible, the operator can select whether to display the image for two-dimensional display or to display the image for three-dimensional display, to thereby enable the image more suitable for observation to be displayed on the monitor.

Modified Example of the Second Embodiment

In the second embodiment, when the determination section 95 determines that the fixed focus objective optical system 51 is focused on the observation site, the message M informing that display of the image for three-dimensional display is enabled is displayed on the monitor 5. However, when the determination section 95 determines that the fixed focus objective optical system 51 is focused on the observation site, the variable focus objective optical system 41 may be automatically switched to the near point observation state, and the display on the monitor 5 may be switched from the image for two-dimensional display to the image for three-dimensional display.

When the determination section 95 determines that the fixed focus objective optical system 51 is focused on the observation site, the control section 93 causes the movable lens 44 to move to a predetermined position close to the image pickup section 61 and transmits the control signal for bringing the variable focus objective optical system 41 into the near point observation state to the focus adjustment section 71.

When receiving the control signal from the control section 93, the focus adjustment section 71 causes the movable lens 44 to the position closest to the image pickup section 61, to bring the variable focus objective optical system 41 into the near point observation state. Then, the image pickup section 61 acquires images with parallax from the variable focus objective optical system 41 and the fixed focus objective optical system 51 to pick up the images, and output image pickup signals to the CCU 92.

The CCU 92 converts the image pickup signals acquired from the image pickup section 61 into signals of images and outputs the signals of the images to the control section 93.

The control section 93 transmits the control signal instructing the generation of the image for three-dimensional display, the signal of the image acquired by the variable focus objective optical system 41, and the signal of the image acquired by the fixed focus objective optical system 51 to the image signal generation output section 94. The image signal generation output section 94 generates the signal of the image for three-dimensional display based on the signals received from the control section 93, to output the generated signal of the image for three-dimensional display to the monitor 5.

With such a configuration, in the case where the operator grasps in advance an observation site which he or she desires to observe with the image for three-dimensional display, when the fixed focus objective optical system 51 is brought close to the observation site and arranged at a focusable position, the determination section 95 determines that the fixed focus objective optical system 51 is focused on the observation site, and the display is automatically switched to the image for three-dimensional display. Thus, the operation is easy, and quick switching to the image for three-dimensional display is possible.

As described above, the first embodiment, the second embodiment, and the modified example are capable of providing the stereoscopic endoscope apparatus that is capable of changing the focal length and performing observation with stereoscopic viewing at a near point.

Note that, in the first embodiment, the second embodiment, and the modified example, the image pickup section 61 is configured of one image pickup device. However, the image pickup section 61 may include two image pickup devices including an image pickup device for the variable focus objective optical system 41 and an image pickup device for the fixed focus objective optical system 51.

Note that, in the first embodiment, the second embodiment, and the modified example, the focus adjustment section 71 includes an electric actuator and is configured to move the movable lens electrically. However, the focus adjustment section 71 may be configured to move the movable lens manually, that is, with the power generated by manually operating the operation lever 32.

In the first embodiment, the second embodiment, and the modified example, the variable focus objective optical system 41 adjusts the position of the movable lens 44 to thereby be capable of changing the focal length to a predetermined focal length. However, the variable focus objective optical system may be switched to a focal length at the time of far point observation (far point observation state) or to a focal length at the time of near point observation (near point observation state). When the variable focus objective optical system 41 is in the far point observation state, the image signal generation output section 94 outputs to the monitor 5 the signal of the intra-subject image acquired by the variable focus objective optical system 41 for displaying the image for two-dimensional display. In addition, when the variable focus objective optical system 41 is in the near point observation state, the image signal generation output section 94 outputs to the monitor 5 the signal of the intra-subject images acquired by the variable focus objective optical system 41 and the fixed focus objective optical system 51 for displaying the image for three-dimensional display. Such a configuration enables prompt switching from the far point observation state to the near point observation state, which results in reduction of time required for changing the focal length.

In the first embodiment, the second embodiment, and the modified example, when the variable focus objective optical system 41 is in the middle-far point observation state, the control section 93 is configured not to transmit the image acquired by the fixed focus objective optical system 51 to the image signal generation output section 94, but the control section 93 may be configured to transmit also the signal of the image acquired by the fixed focus objective optical system 51 to the image signal generation output section 94, and the image signal generation output section 94 may be configured not to output the signal of the image acquired by the fixed focus objective optical system 51 to the monitor.

In the first embodiment, the second embodiment, and the modified example, when the variable focus objective optical system 41 is in the near point observation state, the image signal generation output section 94 outputs the signal of the image acquired by the variable focus objective optical system 41 and the signal of the image acquired by the fixed focus objective optical system 51 as the signal of the image for three-dimensional display. After the signals of the respective images are outputted from the image signal generation output section 94, only the image acquired by the variable focus objective optical system 41 may be displayed on the monitor 5 as the image for two-dimensional display by using a switcher, not shown, provided between the image signal generation output section 94 and the monitor 5, or using a function of the monitor 5.

In the first embodiment, the second embodiment, and modified example, when the image for two-dimensional display is displayed, the signal of the image for two-dimensional display including the image for right eye C1 and the image for left eye C2 is generated from the image acquired by the variable focus objective optical system 41, to output the generated signal of the image for two-dimensional display to the monitor 5. The signal of the image acquired by the variable focus objective optical system 41 may be directly transmitted to and displayed on the monitor 5, without generating the signal of the image for right eye C1 and image for the left eye C2. With such a configuration, the operator can observe the image for two-dimensional display with the stereoscopic viewing glasses put off. When the display is switched from the image for two-dimensional display to the image for three-dimensional display, the setting of the monitor 5 is switched so as to display the image for three-dimensional display, and the operator puts on the stereoscopic viewing glasses to observe the image for three-dimensional display.

The present invention is not limited to the above-described embodiments, and various changes and modifications are possible without changing the gist of the present invention.

With the present invention, it is possible to provide the stereoscopic endoscope apparatus capable of changing the focal length and performing observation with stereoscopic viewing at a near point.

What is claimed is:

1. A stereoscopic endoscope apparatus comprising:
an insertion portion to be inserted into a subject;
a variable focus objective optical system arranged in a distal end portion of the insertion portion, a focal length of the variable focus objective optical system being changeable between a far point observation state and a near point observation state, the variable focus objective optical system forming an optical image of the subject;
a fixed focus objective optical system arranged in the distal end portion of the insertion portion, a focal length of the fixed focus objective optical system being fixed to a focal length equal to the focal length of the variable focus objective optical system in the near point observation state, the fixed focus objective optical system forming an optical image having parallax with respect to the optical image formed by the variable focus objective optical system in the near point observation state;
an image pickup sensor that picks up the optical image formed by the variable focus objective optical system and the optical image formed by the fixed focus objective optical system;
a processor comprising hardware, the processor being configured to:
output an image signal for two-dimensional display generated based on an image pickup signal obtained by picking up the optical image formed by the variable focus objective optical system by the image pickup sensor when the focal length of the variable focus objective optical system and the focal length of the fixed focus objective optical system are different from each other, and
output an image signal for stereoscopic observation generated based on both the image pickup signal obtained by picking up the optical image formed by the variable focus objective optical system by the image pickup sensor and an image pickup signal obtained by picking up the optical image formed by the fixed focus objective optical system by the image pickup sensor when the focal length of the variable focus objective optical system and the focal length of the fixed focus objective optical system are coincident with each other in the near point observation state.

2. The stereoscopic endoscope apparatus according to claim 1, wherein the processor outputs an intra-subject image acquired by the variable focus objective optical system as an image signal when the focal length of the variable focus objective optical system is the focal length in the far point observation.

3. The stereoscopic endoscope apparatus according to claim 1, wherein the variable focus objective optical system comprises a movable lens.

4. The stereoscopic endoscope apparatus according to claim 3, further comprising a focus adjustment actuator that changes the focal length of the variable focus objective optical system, the focus adjustment actuator being connected to the movable lens.

5. The stereoscopic endoscope apparatus according to claim 4, wherein the processor determines the focal length of the variable focus objective optical system, and the focal length of the variable focus objective optical system, to determine that the focal length of the variable focus objective optical system and the focal length of the fixed focus objective optical system are coincident with each other.

6. The stereoscopic endoscope apparatus according to claim 4, wherein, based on the image signal acquired by the fixed focus objective optical system of the image signals outputted from the image pickup sensor, the processor determines whether the fixed focus objective optical system is in focus.

7. The stereoscopic endoscope apparatus according to claim 5, wherein the processor notifies that a stereoscopic observation is available when the focal length of the variable focus objective optical system and the focal length of the fixed focus objective optical system are coincident with each other.

8. The stereoscopic endoscope apparatus according to claim 5, wherein, when the focal length of the variable focus objective optical system and the focal length of the fixed focus objective optical system are coincident with each other, the processor automatically outputs the image signal for stereoscopic observation.

9. The stereoscopic endoscope apparatus according to claim 5, wherein, when determination is made that the fixed focus objective optical system is in focus, the focal length of the variable focus objective optical system is changed, to make the focal length of the variable focus objective optical system and the focal length of the fixed focus objective optical system coincident with each other.

10. The stereoscopic endoscope apparatus according to claim 1, further comprising a monitor connected to the processor,
wherein when the intra-subject images acquired respectively by the variable focus objective optical system and the fixed focus objective optical system are outputted from the processor, the monitor displays an image for three-dimensional display acquired by the variable focus objective optical system and the fixed focus objective optical system or the image for two-dimensional display acquired by the variable focus objective optical system.

11. An image pickup unit comprising:
a variable focus objective optical system, a focal length of the variable focus objective optical system being changeable between a far point observation state and a near point observation state, the variable focus objective optical system forming an optical image of an object;
a fixed focus objective optical system, a focal length of the fixed focus objective optical system being fixed to a focal length equal to the focal length of the variable focus objective optical system in the near point observation state,
the fixed focus objective optical system forming an optical image having parallax with respect to the optical image formed by the variable focus objective optical system in the near point observation state;
an image pickup sensor that picks up the optical image formed by the variable focus objective optical system and the optical image formed by the fixed focus objective optical system;
an image signal generation output processor comprising hardware, the image signal generation output processor being configured to:
output an image signal for two-dimensional display generated based on an image pickup signal obtained by picking up the optical image formed by the variable focus objective optical system by the image pickup sensor when the focal length of the variable focus objective optical system and the focal length of the fixed focus objective optical system are different from each other, and output an image signal for stereoscopic observation generated based on both the image pickup signal obtained by picking up the optical image formed by the variable focus objective optical system by the image pickup sensor and an image pickup signal obtained by picking up the optical image formed by the fixed focus objective optical system by the image pickup sensor when the focal length of the variable focus objective optical system and the focal length of the fixed focus objective optical system are coincident with each other in the near point observation state.

\* \* \* \* \*